US006679916B1

(12) United States Patent
Frankle et al.

(10) Patent No.: US 6,679,916 B1
(45) Date of Patent: Jan. 20, 2004

(54) SHOULDER PROSTHESIS SYSTEM

(76) Inventors: Mark A. Frankle, 5124 Longfellow Ave., Tampa, FL (US) 33629; Dennis Moad, 9800 Metric Blvd., Austin, TX (US) 78758

( * ) Notice: Subject to any disclaimer, the term of this patent is extended or adjusted under 35 U.S.C. 154(b) by 56 days.

(21) Appl. No.: 10/134,299

(22) Filed: Apr. 29, 2002

(51) Int. Cl.[7] .................................................. A61F 2/40
(52) U.S. Cl. ..................................................... 623/19.12
(58) Field of Search .......................... 623/19.11, 19.12, 623/19.13, 19.14

(56) References Cited

U.S. PATENT DOCUMENTS

D285,968 S  *  9/1986  Kinnett .......................... D24/33
5,080,673 A  *  1/1992  Burkhead et al. ........... 623/19.11
5,489,310 A  *  2/1996  Mikhail ...................... 623/19.11

* cited by examiner

Primary Examiner—Eduardo C. Robert
(74) Attorney, Agent, or Firm—Edward P. Dutkiewicz

(57) ABSTRACT

A shoulder prosthesis system has a glenoid socket with an interior face with couplers and an exterior face being a concave articulating face with a first longitudinal radius of curvature and a second latitudinal radius of curvature. A backing plate has an outer extent and an inner extent. The outer extent has a cylindrical base and a recess around the periphery and a plurality of tapered bores extending through the outer extent spaced between the recess and the center of the backing plate. The inner extent is formed with a projection with threads adapted to be rotatably coupled into a scapula of a patient. The couplers of the outer extent are adapted to snap couple with the recesses of the glenoid socket.

5 Claims, 3 Drawing Sheets

SHOULDER PROSTHESIS SYSTEM

BACKGROUND OF THE INVENTION

1. Field of the Invention

The present invention relates to a shoulder prosthesis system and more particularly pertains to a shoulder prosthesis system with improved fabrication, installation and utilization characteristics.

2. Description of the Prior Art

The use of prosthesis systems is known in the prior art. More specifically, prosthesis systems of known designs and configurations previously devised and utilized for the purpose of improving various characteristics of prostheses through conventional methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,944,757 to Grammont discloses a total trochitero-acromial shoulder prosthesis. U.S. Pat. No. 4,550,450 to Kinnett discloses a total shoulder prosthesis system. U.S. Pat. No. 5,080,673 to Burkhead et al. discloses a glenoid prosthesis and method of use. Frankly, U.S. Pat. No. 5,593,448 to Dong discloses a glenoid component for shoulder prosthesis and implant method.

While these devices fulfill their respective, particular objectives and requirements, the aforementioned patents do not describe a shoulder prosthesis system with the improved fabrication, installation and utilization characteristics of the present invention.

In this respect, the shoulder prosthesis system according to the present invention substantially departs from the conventional concepts and designs of the prior art, and in doing so provides an apparatus primarily developed for the purpose of improving the fabrication, installation and utilization of a shoulder prosthesis.

Therefore, it can be appreciated that there exists a continuing need for a new and improved shoulder prosthesis system which can be used to improve the fabrication, installation and utilization of a shoulder prosthesis. In this regard, the present invention substantially fulfills this need.

SUMMARY OF THE INVENTION

In view of the foregoing disadvantages inherent in the prosthesis systems now present in the prior art, the present invention provides an improved shoulder prosthesis system. As such, the general purpose of the present invention, which will be described subsequently in greater detail, is to provide a new and improved shoulder prosthesis system and method which has all the advantages of the prior art and none of the disadvantages.

To attain this, the present invention essentially comprises a glenoid socket. The glenoid socket is fabricated of ultra high molecular weight polyethylene in a generally disk-like configuration and has a diameter of about 1.260 inches. The socket has an interior face and an exterior face. The exterior face is a concave articulating face. This articulating face has a depth of about 0.198 inches and a first longitudinal radius of curvature measuring about 1.100 inches and a second latitudinal radius of curvature measuring about 1.340 inches. The interior face has six equally spaced L-shaped couplers. The couplers have edges extending radially outwardly around the periphery. The edges provide bearing surfaces for allowing the glenoid socket with its L-shaped couplers to join with the backing plate as will be later described. A central hexagonal post extends perpendicularly from the center of the interior face. The exterior face is adapted to articulate with a head of a humerus of a patient.

Next, a backing plate is provided. The backing plate is fabricated of titanium. The backing plate is in a generally disk-like configuration and has an outer extent and an inner extent. The outer extent has a cylindrical base with a diameter measuring about 1.260 inches. An L-shaped recess around the periphery of the outer extent and a central hexagonal bore are provided. Four tapered bores extend through the outer extent and are spaced between the L-shaped recess and the hexagonal central bore. The inner extent is formed with a projection with a male Morse taper with threads adapted to be rotatably coupled into a scapula of a patient. The L-shaped couplers of the outer extent are adapted to snap couple with the L-shaped recesses of the glenoid socket together forming a prosthetic glenoid cavity adapted to articulate with the humerus.

Lastly, four screws are provided. The screws extend through the four tapered bores of the backing plate. The screws are adapted to be rotatably coupled into the scapula around, and parallel with, the projection.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved shoulder prosthesis system which has all of the advantages of the prior art prosthesis systems of known designs and configurations and none of the disadvantages.

It is a further object of the present invention to provide a new and improved shoulder prosthesis system which is of durable and reliable constructions.

Even still another object of the present invention is to provide a system for improving the fabrication, installation and utilization characteristics of a shoulder prosthesis.

Lastly, it is an object of the present invention to provide a new and improved shoulder prosthesis system having a glenoid socket with an interior face with couplers and an exterior face being a concave articulating face with a first longitudinal radius of curvature and a second latitudinal radius of curvature, a backing plate with an outer extent having a cylindrical base and a recess around the periphery and a plurality of tapered bores extending there through spaced between the recess and the center of the backing plate, an inner extent is formed with a projection with threads adapted to be rotatably coupled into a scapula of a patient, and couplers of the outer extent adapted to snap couple with the recesses of the glenoid socket.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figures 1, 2:
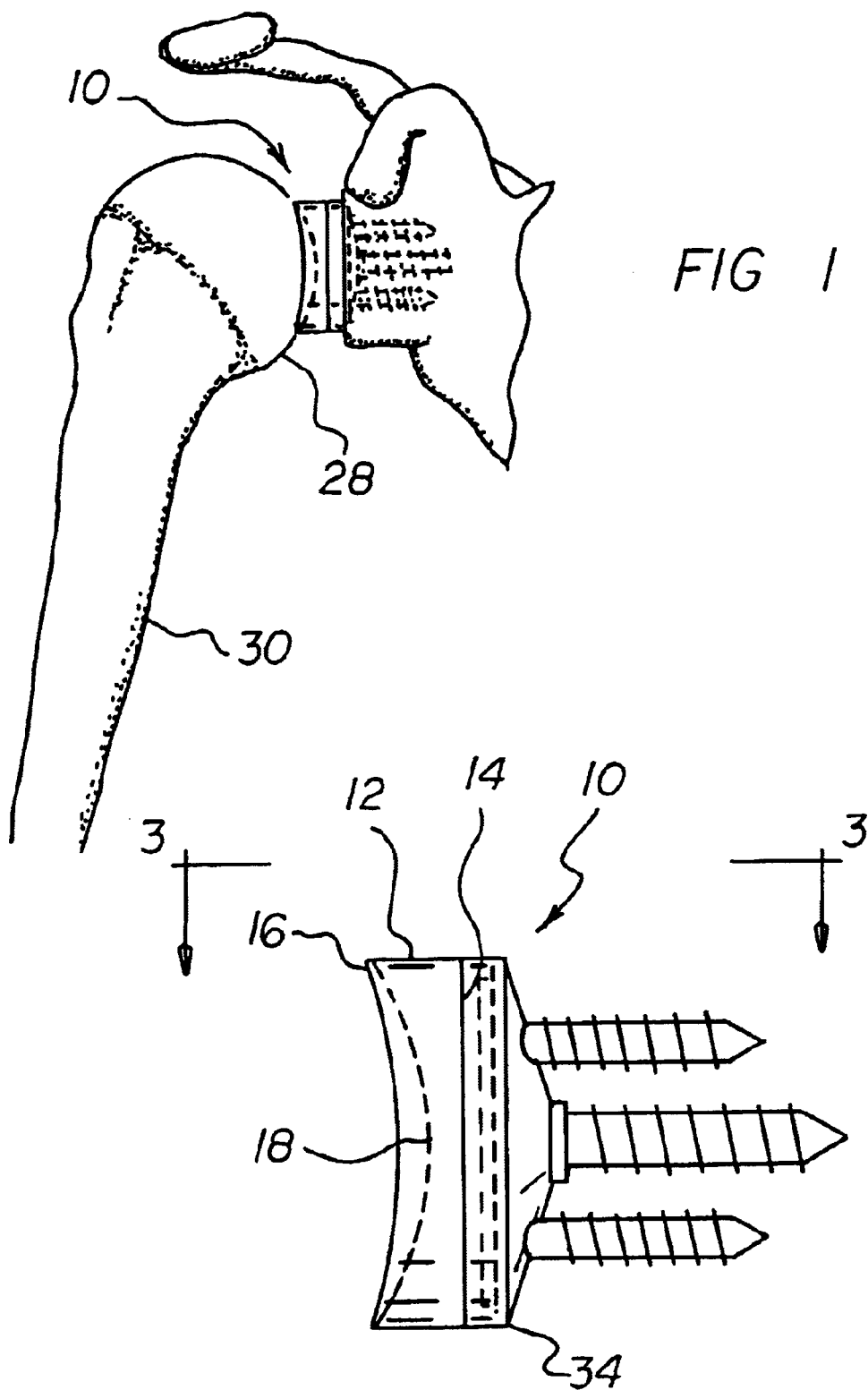
FIG. 1 is a front elevational view of the shoulder prosthesis system constructed in accordance with the principles of the present invention.
FIG. 2 is an enlarged showing of the shoulder prosthesis system of FIG. 1 but with the associated bones removed.
Figures 3, 4, 5:
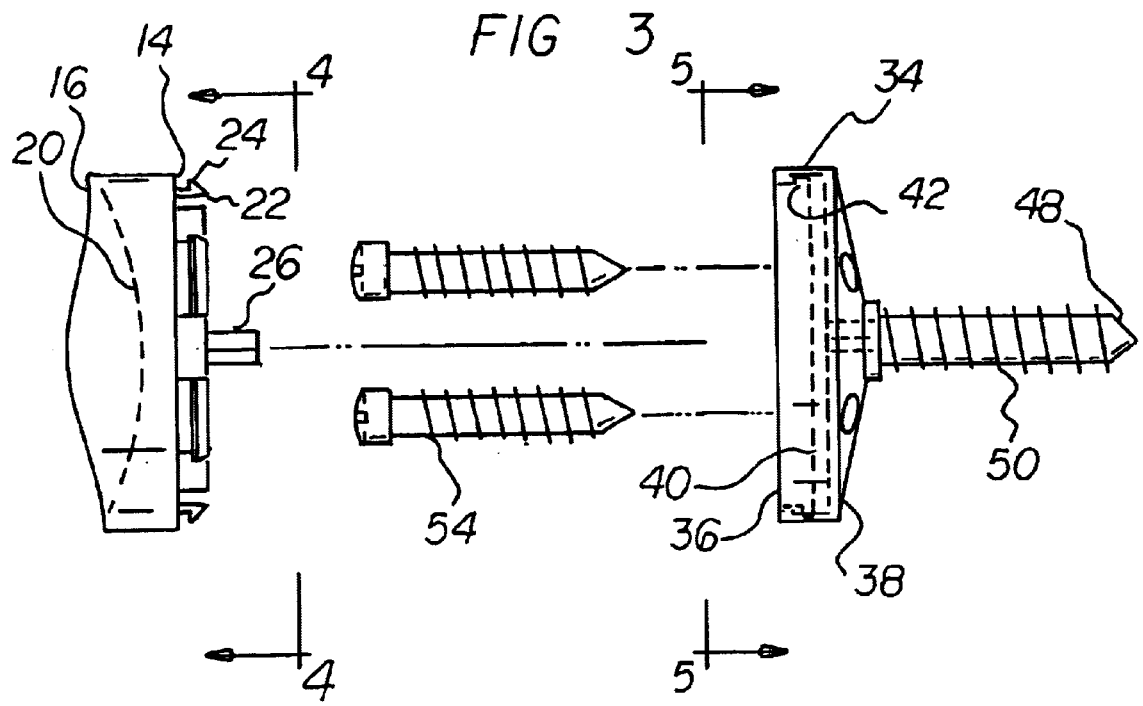
FIG. 3 is a top elevational view taken along line 3—3 of FIG. 2.
FIG. 4 is a front elevational view taken along line 4—4 of FIG. 3.
FIG. 5 is a front elevational view taken along line 5—5 of FIG. 3.

With reference now to the drawings, and in particular to FIG. 1 thereof, the preferred embodiment of the new and improved shoulder prosthesis system embodying the principles and concepts of the present invention and generally designated by the reference numeral 10 will be described.

The present invention, the shoulder prosthesis system 10 is comprised of a plurality of components. Such components in their broadest context include a glenoid socket and a backing plate. Such components are individually configured and correlated with respect to each other so as to attain the desired objective.

First provided is a glenoid socket 12. The glenoid socket is fabricated of ultra high molecular weight polyethylene in a generally disk-like configuration and has a diameter of about 1.260 inches. The socket has an interior face 14 and an exterior face 16. The exterior face is a concave articulating face. The articulating face has a depth of about 0.198 inches and a first longitudinal radius of curvature 18 measuring about 1.100 inches and a second latitudinal radius of curvature 20 measuring about 1.340 inches. The interior face has six equally spaced L-shaped couplers 22. The couplers have edges 24 extending radially outwardly around the periphery. The edges 24 provide bearing surfaces for allowing the glenoid socket with its L-shaped couplers to join with the backing plate as will be later described. A central hexagonal post 26 extends perpendicularly from the center of the interior face. The exterior face is adapted to articulate with a head 28 of a humerus 30 of a patient.

Figure 6:
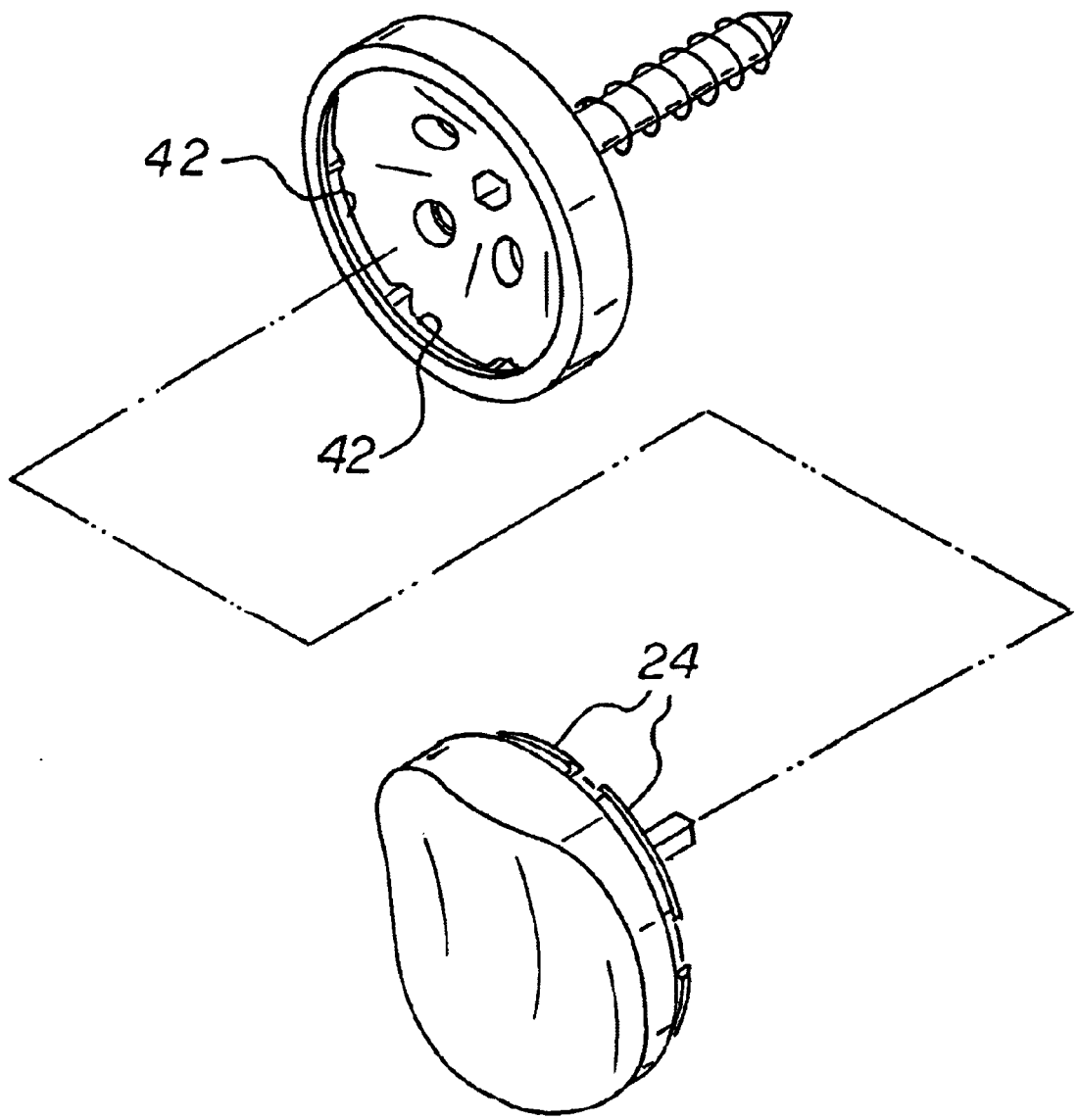
FIG. 6 is an exploded perspective view of the system constructed in accordance with the principles of the present invention.

Next, a backing plate 34 is provided. The backing plate is fabricated of titanium. The backing plate is in a generally disk-like configuration and has an outer extent 36 and an inner extent 38. The outer extent has a cylindrical base 40 with a diameter measuring about 1.260 inches. An L-shaped recess 42 around the periphery of the outer extent and a central hexagonal bore 44 are provided. Four tapered bores 46 extend through the outer extent and are spaced between the L-shaped recess and the hexagonal central bore. The inner extent is formed with a projection 48 with a male Morse taper with threads 50 adapted to be rotatably coupled into a scapula of a patient. As can be seen in FIG. 6, the L-shaped couplers of the outer extent are adapted to snap couple with the L-shaped recesses of the glenoid socket so that they together form a prosthetic glenoid cavity adapted to articulate with the humerus.

Lastly, four screws 54 are provided. The screws extend through the four tapered bores of the backing plate. The screws are adapted to be rotatably coupled into the scapula around and parallel with the projection. The outer extent is snap coupled with the glenoid socket after the four screws are in place.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A shoulder prosthesis system for providing a shoulder prosthesis with improved fabrication, installation and utilization characteristics comprising, in combination;

a glenoid socket fabricated of ultra high molecular weight polyethylene in a generally disk-like configuration having a diameter of about 1.260 inches, the socket having an interior face and an exterior face, the exterior face being a concave articulating face having a depth of about 0.198 inches and having a first longitudinal radius of curvature measuring about 1.100 inches and a second latitudinal radius of curvature measuring about 1.340 inches, the interior face having six equally spaced L-shaped couplers with edges extending radially outwardly around the periphery and a central hexagonal post extending perpendicularly from the center of the interior face, the exterior face being adapted to articulate with a head of a humerus of a patient;

a backing plate fabricated of titanium in a generally disk-like configuration having an outer extent and an inner extent, the outer extent having a cylindrical base with a diameter measuring about 1.260 inches and having an L-shaped recess around the periphery of the outer extent, a central hexagonal bore, and four tapered bores extending through the outer extent being spaced between the L-shaped recess and the hexagonal central bore, the inner extent being formed with a projection with a male Morse taper with threads adapted to be rotatably coupled into a scapula of a patient, the L-shaped couplers of the outer extent adapted to snap couple with the L-shaped recesses of the glenoid socket together forming a prosthetic glenoid cavity adapted to articulate with the humerus; and four screws extending through the four tapered bores of the backing plate adapted to be rotatably coupled into the scapula around and parallel with the projection.

2. A shoulder prosthesis system comprising:

a glenoid socket having an interior face having couplers and an exterior face being a concave articulating face having a first longitudinal radius of curvature and a second latitudinal radius of curvature; and a backing plate having an outer extent, an inner extent, and a center, the outer extent having a cylindrical base and a recess around the periphery and a plurality of tapered bores extending there through and spaced between the recess and the center, the inner extent being formed with a projection with threads adapted to be rotatably coupled into a scapula of a patient, the couplers of the outer extent adapted to snap couple with the recesses of the glenoid socket.

3. The system as set forth in claim 2 wherein the glenoid socket is fabricated of ultra high molecular weight polyethylene.

4. The system as set forth in claim 2 wherein the backing plate is fabricated of titanium.

5. The system as set forth in claim 2 and further including a central hexagonal post extending perpendicularly from the center of the interior face and a central hexagonal bore in the outer extent.

\* \* \* \* \*

UNITED STATES PATENT AND TRADEMARK OFFICE
CERTIFICATE OF CORRECTION

PATENT NO.     : 6,679,916 B1
DATED          : January 20, 2004
INVENTOR(S)    : Frankle et al.

It is certified that error appears in the above-identified patent and that said Letters Patent is hereby corrected as shown below:

<u>Title page,</u>
Item [75], Inventor, "Moad" name should read as
-- Dennis C. Moad
   906 San Jacinto Street
   Lockhart, TX (US) 78644 --

Signed and Sealed this

Twenty-fifth Day of May, 2004

JON W. DUDAS
*Acting Director of the United States Patent and Trademark Office*